(12) United States Patent
Hawkins et al.

(10) Patent No.: US 10,032,236 B2
(45) Date of Patent: Jul. 24, 2018

(54) ELECTRONIC HEALTH RECORD TIMELINE AND THE HUMAN FIGURE

(75) Inventors: Michael Hawkins, Hoboken, NJ (US);
Dmitry Pavlov, New Paltz, NY (US);
Christopher Burt, Warwick, NY (US);
Kenneth Lopez, New York, NY (US);
Khan Siddiqui, Highland, MD (US)

(73) Assignee: General Electric Company, Schenectady, NY (US)

(*) Notice: Subject to any disclaimer, the term of this patent is extended or adjusted under 35 U.S.C. 154(b) by 531 days.

(21) Appl. No.: 12/323,033

(22) Filed: Nov. 25, 2008

(65) Prior Publication Data

US 2009/0192823 A1   Jul. 30, 2009

Related U.S. Application Data

(63) Continuation-in-part of application No. 12/110,053, filed on Apr. 25, 2008.
(Continued)

(51) Int. Cl.
*A61B 5/00* (2006.01)
*G06F 19/00* (2018.01)
(Continued)

(52) U.S. Cl.
CPC ........... *G06Q 50/22* (2013.01); *G06F 19/321* (2013.01); *G06Q 10/06* (2013.01); *G06Q 50/24* (2013.01); *G16H 10/60* (2018.01); *G16H 15/00* (2018.01)

(58) Field of Classification Search
CPC ....... G06F 19/322; G06Q 50/24; G06Q 50/22
(Continued)

(56) References Cited

U.S. PATENT DOCUMENTS 5,920,317 A * 7/1999 McDonald ..................... 715/853
6,006,126 A * 12/1999 Cosman ......................... 600/426
(Continued)

OTHER PUBLICATIONS

Non-final office action, issued by the United States Patent and Trademark Office in connection with U.S. Appl. No. 12/110,053, dated May 27, 2011, 9 pages.
(Continued)

*Primary Examiner* — Elaine Gort
*Assistant Examiner* — Trang T Nguyen
(74) *Attorney, Agent, or Firm* — Hanley, Flight and Zimmerman, LLC

(57) ABSTRACT

A patient information interface system presents an aggregated, graphical view of patient anatomy and history. The system includes a graphical representation of at least a portion of a human anatomy including one or more indicators, aggregated from a plurality of clinical information sources and located at anatomical locations on the representation, that correspond to clinical events that have occurred in connection with a patient. The system also includes an electronic health record timeline of clinical events for the patient. The timeline includes the same one or more indicators that are displayed on the graphical representation corresponding to clinical events that have occurred in connection with a patient. A selection or change of an indicator on one of the graphical representation or the electronic health record timeline triggers a corresponding selection or change of the indicator on the other of the graphical representation or the electronic health record timeline.

20 Claims, 6 Drawing Sheets

Related U.S. Application Data

(60) Provisional application No. 60/926,356, filed on Apr. 26, 2007.

(51) Int. Cl.

| | | |
|---|---|---|
| *G06Q 50/22* | (2018.01) | |
| *G06Q 10/06* | (2012.01) | |
| *G06Q 50/24* | (2012.01) | |
| *G16H 10/60* | (2018.01) | |
| *G16H 15/00* | (2018.01) | |

(58) Field of Classification Search
USPC .......................................................... 705/3, 2
See application file for complete search history.

(56) References Cited

U.S. PATENT DOCUMENTS

| | | | |
|---|---|---|---|
| 7,038,588 B2 | 5/2006 | Boone et al. | |
| 7,890,498 B1* | 2/2011 | Hafey et al. ................. 707/722 |
| 7,899,687 B2 | 3/2011 | Morris | |
| 8,090,742 B2 | 1/2012 | Mok et al. | |
| 8,140,352 B2 | 3/2012 | Johnson et al. | |
| 2001/0041992 A1* | 11/2001 | Lewis et al. ..................... 705/3 |
| 2001/0051881 A1* | 12/2001 | Filler ................................ 705/3 |
| 2002/0075293 A1* | 6/2002 | Charisius et al. ............. 345/704 |
| 2002/0091309 A1* | 7/2002 | Auer .............................. 600/300 |
| 2002/0156909 A1* | 10/2002 | Harrington ................... 709/231 |
| 2003/0065589 A1* | 4/2003 | Giacchetti ....................... 705/27 |
| 2003/0146942 A1* | 8/2003 | Helgason et al. ............. 345/968 |
| 2004/0087839 A1* | 5/2004 | Raymond et al. ............ 600/300 |
| 2004/0102706 A1* | 5/2004 | Christopher et al. ......... 600/453 |
| 2005/0283387 A1* | 12/2005 | Donoghue et al. ............... 705/3 |
| 2006/0085223 A1* | 4/2006 | Anderson et al. ................ 705/2 |
| 2006/0199167 A1* | 9/2006 | Yang et al. .................... 434/365 |
| 2006/0265249 A1* | 11/2006 | Follis et al. ...................... 705/3 |
| 2007/0027736 A1* | 2/2007 | Reynolds et al. ................ 705/8 |
| 2007/0094197 A1* | 4/2007 | Datena et al. .................. 706/46 |
| 2008/0183074 A1* | 7/2008 | Carls et al. ................... 600/429 |
| 2008/0208631 A1* | 8/2008 | Morita et al. ..................... 705/3 |
| 2008/0281637 A1 | 11/2008 | Matz | |
| 2009/0003669 A1* | 1/2009 | Parks ..................... A61B 5/037 |
| | | | 382/128 |
| 2009/0037223 A1* | 2/2009 | Green ................... G06F 19/322 |
| | | | 705/3 |
| 2009/0222286 A1 | 9/2009 | Elsholz | |
| 2009/0228299 A1* | 9/2009 | Kangarloo et al. ............... 705/2 |
| 2009/0317781 A1* | 12/2009 | Oosthuizen ................... 434/267 |
| 2011/0246225 A1 | 10/2011 | Green, III et al. | |

OTHER PUBLICATIONS

Final rejection, issued by the United States Patent and Trademark Office in connection with U.S. Appl. No. 12/110,053, dated Nov. 3, 2011, 11 pages.

Advisory action, issued by the United States Patent and Trademark Office in connection with U.S. Appl. No. 12/110,053, dated Feb. 16, 2012, 6 pages.

Non-final office action, issued by the United States Patent and Trademark Office in connection with U.S. Appl. No. 12/110,053, dated Mar. 30, 2012, 12 pages.

Final rejection, issued by the United States Patent and Trademark Office in connection with U.S. Appl. No. 12/110,053, dated Sep. 7, 2012, 13 pages.

\* cited by examiner

FIG. 1

ELECTRONIC HEALTH RECORD TIMELINE AND THE HUMAN FIGURE

RELATED APPLICATIONS

The present application claims the benefit of priority as a continuation-in-part to U.S. patent application Ser. No. 12/110,053, filed on Apr. 25, 2008, entitled "Systems and Methods for Presentation of Clinical Evidence for Diagnostic Interpretation," which claims the benefit of priority to U.S. Provisional Application No. 60/926,356, filed on Apr. 26, 2007, entitled "Special Methodics for Optimal Presentation of the Clinical Evidences for Diagnostic Interpretation", each of which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

FIELD OF INVENTION

The presently described technology relates to graphical display of patient information. More specifically, the presently described technology relates to aggregation and graphical display of patient information in a single interface.

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

It is now a common practice that medical imaging devices produce diagnostic images in a digital representation. The digital representation typically includes a two dimensional raster of the image equipped with a header. The header includes collateral information with respect to the image itself, patient demographics, imaging technology and other data important for proper presentation and diagnostic interpretation of the image. Often, diagnostic images are grouped in series. Each series represents images that have something in common while differing in details—for example, images representing anatomical cross-sections of a human body substantially normal to its vertical axis and differing by their position on that axis from top to bottom are grouped in an axial series. A single medical exam, often referred to as a "Study" or "Exam", often includes several series of images—for example, images exposed before and after injection of contrast material or by images with different orientation or differing by any other relevant circumstance(s) of imaging procedure.

Digital images are forwarded to specialized archives equipped with proper hardware and/or software for safe storage, search, access and distribution of the images and collateral information required for successful diagnostic interpretation. An information system controlling the storage is aware of multiple current and historical medical exams carried over for the same patient, diagnostic reports rendered on the basis of the exams, and, through its interconnectivity to other information systems, can posses the knowledge of other existing clinical evidences stored on, or acquired from, the other information systems. Such evidence can be further referred as "collateral clinical evidence."

Additionally, in diagnostic reading, rendering a diagnostic report is based not only on the newly acquired diagnostic images but also involves analysis of other current and prior clinical information, including but not limited to prior medical imaging exams. In recent history, a reading physician was naturally limited to few sources of such clinical data including probably a film jacket of one to three prior studies and other clinical evidence printed on an exam requisition form.

However, with an information revolution extending into healthcare enterprises, practically all clinical evidence is subject to storage and presentation through various information systems—sometimes accessed in separate systems, but more and more integrated for cross-system search and retrieval. Such principal availability of extensive clinical history presents a serious challenge to ergonomic design of diagnostic workstations that allow easy and effective search and navigation within a multiplicity of clinical evidence to facilitate productivity of diagnostic reading without risk of missing an important piece of clinical evidence which loss or neglecting can substantially change diagnostic conclusion or affect important details of a diagnostic report.

BRIEF SUMMARY OF THE INVENTION

Certain embodiments of the present invention provide systems and methods for presentation of clinical evidence to a user.

Certain embodiments provide a patient information interface system presenting an aggregated, graphical view of patient anatomy and history. The system includes a graphical representation of at least a portion of a human anatomy including one or more indicators corresponding to clinical events that have occurred in connection with a patient. Each of the one or more indicators is located at an anatomical location on the graphical representation affected by the clinical event corresponding to the indicator. The system also includes an electronic health record timeline of clinical events for the patient. The timeline includes the one or more indicators corresponding to clinical events that have occurred in connection with a patient. The one or more indicators are displayed on both the graphical representation and the electronic health record timeline. The one or more indicators represent clinical event information aggregated from a plurality of clinical information sources. A selection or change of an indicator on one of the graphical representation or the electronic health record timeline triggers a corresponding selection or change of the indicator on the other of the graphical representation or the electronic health record timeline.

Certain embodiments provide a method for aggregating and displaying a graphical view of patient anatomy and history. The method includes compiling patient information from a plurality of clinical information sources and identifying clinical events related to the patient based on the patient information. The method also includes graphically displaying the compiled patient information using both a graphical representation of at least a portion of a human anatomy and an electronic health record timeline of clinical events for the patient. Each of the representation and the timeline include corresponding sets of one or more indicators identifying clinical events that have occurred in connection with the patient. Each of the one or more indicators is located at an anatomical location on the graphical representation affected by the clinical event corresponding to the indicator and located on the timeline at a point in time at which the clinical event occurred. The method further includes facilitating user interaction with the displayed patient clinical event indicators on both the graphical representation and the timeline. A selection or change of an indicator on one of the graphical representation or the electronic health record timeline triggers a corresponding selection or change of the indicator on the other of the graphical representation or the electronic health record timeline.

Certain embodiments provide a machine readable medium having a set of instructions for execution on a computing device. The set of instructions, when executed on the computing device, cause the computing device to execute a method for aggregating and displaying a graphical view of patient anatomy and history. The method includes compiling patient information from a plurality of clinical information sources and identifying clinical events related to the patient based on the patient information. The method also includes graphically displaying the compiled patient information using both a graphical representation of at least a portion of a human anatomy and an electronic health record timeline of clinical events for the patient. Each of the representation and the timeline include corresponding sets of one or more indicators identifying clinical events that have occurred in connection with the patient. Each of the one or more indicators is located at an anatomical location on the graphical representation affected by the clinical event corresponding to the indicator and located on the timeline at a point in time at which the clinical event occurred. The method further includes facilitating user interaction with the displayed patient clinical event indicators on both the graphical representation and the timeline. A selection or change of an indicator on one of the graphical representation or the electronic health record timeline triggers a corresponding selection or change of the indicator on the other of the graphical representation or the electronic health record timeline.

BRIEF DESCRIPTION OF SEVERAL VIEWS OF THE DRAWINGS

FIG. 1 illustrates a graphical workflow manager including a plurality of presentation panes in accordance with an embodiment of the present invention.

Figure 2:
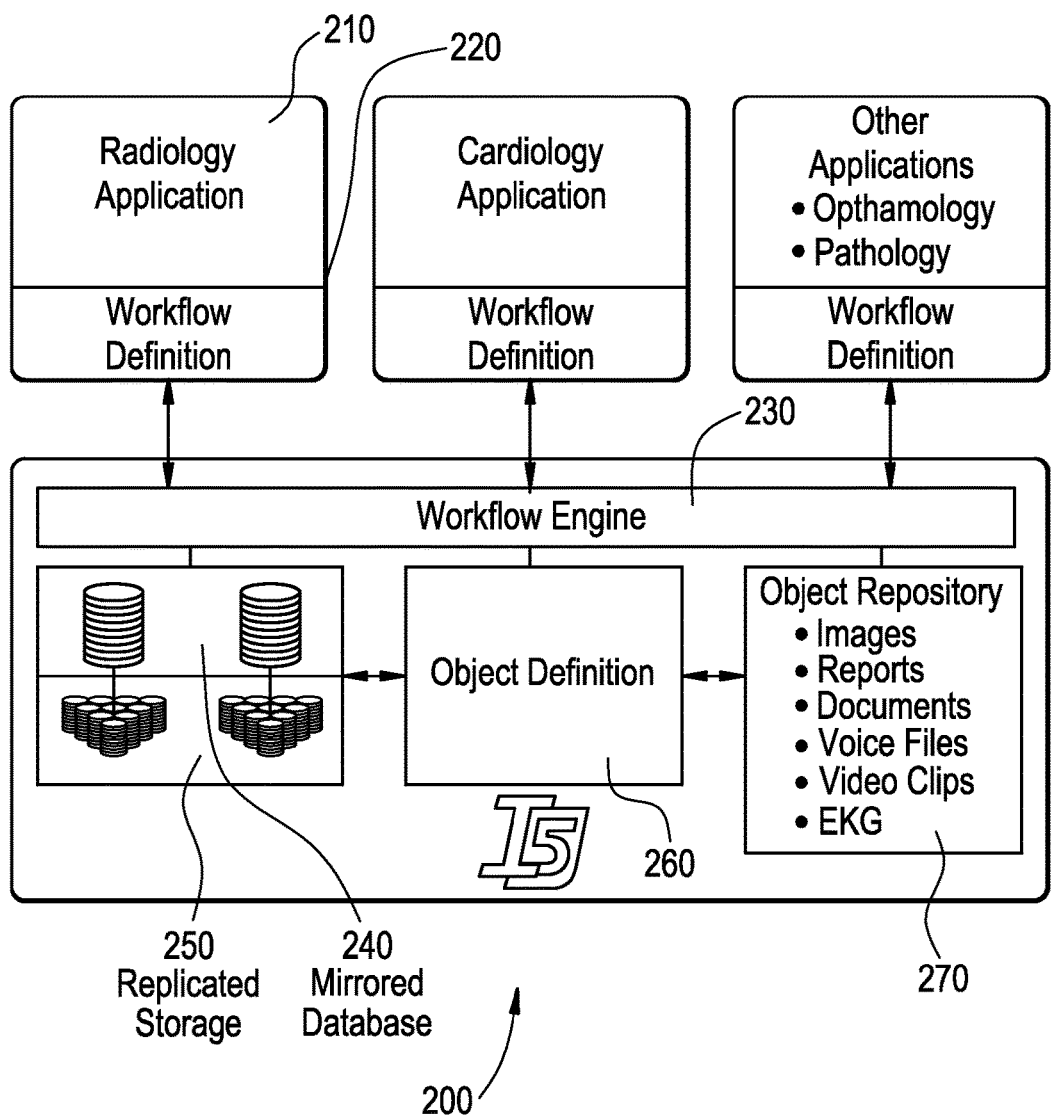
FIG. 2 demonstrates a business and application diagram for PACS information system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide a single view of a patient's full medical record across specialties in an aggregate, graphical format that enables a user to drill down for additional information and to determine severity within an anatomic structure for a patient over time.

In prior systems, users have had difficulty in viewing patient's record even when all data is present. There is no facility for determining severity of chronic patient issues. It has not been easy to see, in a single view, a patient's full health record across specialties. Even when a patient's clinical data is provided, most electronic medical records ("EMRs") or electronic health records ("EHRs") provide separate sections for radiology, cardiology, labs, etc., that are not aggregated in a single view so that you know immediately what's going on with the patient. Prior systems failed to provide a capability to determine a severity within an anatomic structure for a patient by time, for example.

Certain embodiments provide a graphical representation of a patient or portion of the patient anatomy in conjunction with a timeline to graphical illustrate and provide easy, aggregated access to a patient's record information across various sources. Certain embodiments enable a user to grasp the full extent of a patient's current and past health without searching through multiple systems. The representation is a multi-specialty graphical representation of a patient's health record, both anatomic and historical, for example.

A representation of a human figure is provided to illustrate what procedures a patient has undergone, to which anatomical part the procedures were applied, and what pathology was found, for example. Such information can be aggregated from a plurality of sources and shown on an anatomical representation. In certain embodiments, visual indicators, such as dots, icons, highlights, etc., can be used to indicate a data point on the anatomic figure.

For example, a representation can use dots to indicate data points in relation to the anatomy. Each dot indicates a procedure performed at that anatomical location, and a coloration of the dot indicates an outcome or diagnosis (e.g., good, bad, unknown, etc.). A user then can drill down into each dot to obtain an additional level of detail.

In certain embodiments, a user can hover over or click and see a report, image, etc. A user can also see an EHR timeline for the patient to see the dots/outcomes over time. That is, dots and/or other indicators represented on the anatomy can also be provided in an EHR timeline view for user analysis. Together the human figure representation and EHR timeline can serve as an anatomical dashboard. The representation can be a human figure, heart, lung, etc., whatever is appropriate. The representation can be a three-dimensional ("3D") representation of a patient body, certain body part, certain body region, etc. When a user moves a cursor to one dot, the timeline can be scrolled according and vice versa. The timeline can be combined (e.g., overlaid) with the human figure, so the user sees a time series of the body or part itself, for example.

Patient data can be found in a plurality of formats including in Health Level Seven ("HL7") messages, in Digital Imaging Communications in Medicine ("DICOM") data, in structured reports, and in aggregated form, for example. Data can be received from a plurality of clinical information systems, such as a radiology information system ("RIS"), picture archiving and communication system ("PACS"), cardiovascular information system ("CVIS"), EMR, lab, physical exams, etc. Within HL7 messages, for example, a message includes a procedure code, a current procedural terminology ("CPT") code, etc. A CPT code can be grouped by anatomical structure, for example, to indicate a laterality (left, right, etc.).

In mammography, for example, a user may be able to determine a diagnosis using a birads code. In other examples, depending on whether a decision support system is present, suppose a patient had a procedure one and then a procedure two. If a decision support system is present, the decision support system can direct the user to procedure two after procedure one resulted in a positive diagnosis, so the user can deduce that procedure one was a positive diagnosis, for example. If procedure two is not related to procedure one, for example, then the user can probably infer that one is negative because procedure two is going in a different direction. For example, suppose that procedure two is a surgery and procedure one is a positron emission tomography ("PET")—computed tomography ("CT") or PET—CT image, then the user can presume that the surgery is to remove cancer that was identified from a positive diagnosis in procedure one. If procedure two is the same as procedure one but is six months later, for example, then procedure two is probably a follow up for a diagnosis in procedure one.

In certain embodiments, the representation of the human figure includes dots and/or other graphical indicators that are representations of positive or negative outcomes, for example. Dots can also be representations of actual procedures (e.g., electrocardiogram ("EKG") waveforms, x-ray and/or other image thumbnails, reports, charts, etc.). A user can position a cursor over an indicator to show the underlying content of that indicator, and can drill down into the human figure (e.g., drag a displayed cursor across and highlight or box an area and drill in or out of that area based on particular anatomical structures).

Certain embodiments provide methods and systems for presentation, search, discovery, drill down, retrieval, and/or examination of clinical information of various types, nature, and/or time period, which evidence is available in the PACS environment either in its intrinsic storage subsystems or through links to external information clinical systems including but not limited to Radiology Information Systems (RIS), Electronic Medical Records (EMR), Laboratory Information Systems, (RIS) Hospital Information Systems (HIS), Insurance Provider's Information Systems, and/or other archives and information systems, for example.

According to certain embodiments, a workstation screen can be dedicated to support multiple graphical and textual forms of presenting available main and collateral clinical evidence that can be easily searched, discovered, drilled down and retrieved for full blown presentation and analysis either on the same screen or on another screen of the workstation, for example. The specialized screen will be further referred as a "Workflow Screen". The Workflow Screen can include a plurality of "Presentation Panes"—each pane representing a specialized view over the available clinical evidence in various perspectives including but not limited to: historical, anatomical, demographical, administrative, subspecialty, other perspective, and/or through a specialized mix of selected basic perspectives, for example.

According to certain embodiments, the combination of presentation panes can be pre-configured and/or personalized on multiple levels of an enterprise, administrative and/or subspecialty groups, or individual level, for example. The combination of presentation panes and/or behavior of each individual pane can be set to be context sensitive respective to a wide variety of factors including but not limited to patient personalized data, a nature of a medical case, and a current workflow as a whole, for example. One or more panes can adjust to a current step within an overall workflow, for example.

Content of the presentation panes can be synchronized between any two or more panes as part of a customization pattern, and/or by explicit choice of an operator, for example. For purposes of example only, selection of an anatomical region (e.g., an abdominal region) on anatomical presentation pane automatically reduces a list of historical exams to only those prior exams targeted to the selected anatomical part. As another example, a selection of "oncology" from an exam types list will focus primarily on clinical evidence gathered with respect to oncology while leaving other information in close proximity, but probably with less visible details and/or involving a series of actions (e.g., multiple mouse clicks) to be reached/drilled down.

All disclosed embodiments of the present invention can optionally feature the following properties: 1. Each presentation pane can have its different context sensitive graphical user interface ("GUI") controls including but not limited to mouse operational modes, toolbars, right-click menus, others and/or a combination of the above, for example. 2. Graphical and/or overlay elements of each of presentation panes can be clickable and/or otherwise selectable resulting in a certain action happening upon clicking or selecting an element, thus being a special sort of interactive controls, for example.

It should be clear for any person skilled in the art that certain embodiments of the present invention should not be limited only to the multiplicity of disclosed embodiments. Alternatively these embodiments and/or nature of the information system should be considered as a convenient way of presenting basic principles, novelty concepts and inventive steps of certain embodiments of the present invention for the purpose of an application for patent.

Certain embodiments of the present invention are described in conjunction with graphical representation in the drawings. The invention itself should not be limited to the illustrative embodiments only. On the contrary, those embodiments should be regarded as particular examples of interactive systems and methods for effective search, discovery, data mining, drill down, retrieval and/or display for detailed examination of a piece or group of multidisciplinary clinical information for interpretation of examined media to help increase human productivity and interpretation quality, and/or help reduce a risk that an important piece of collateral evidence is missed.

Figure 1:
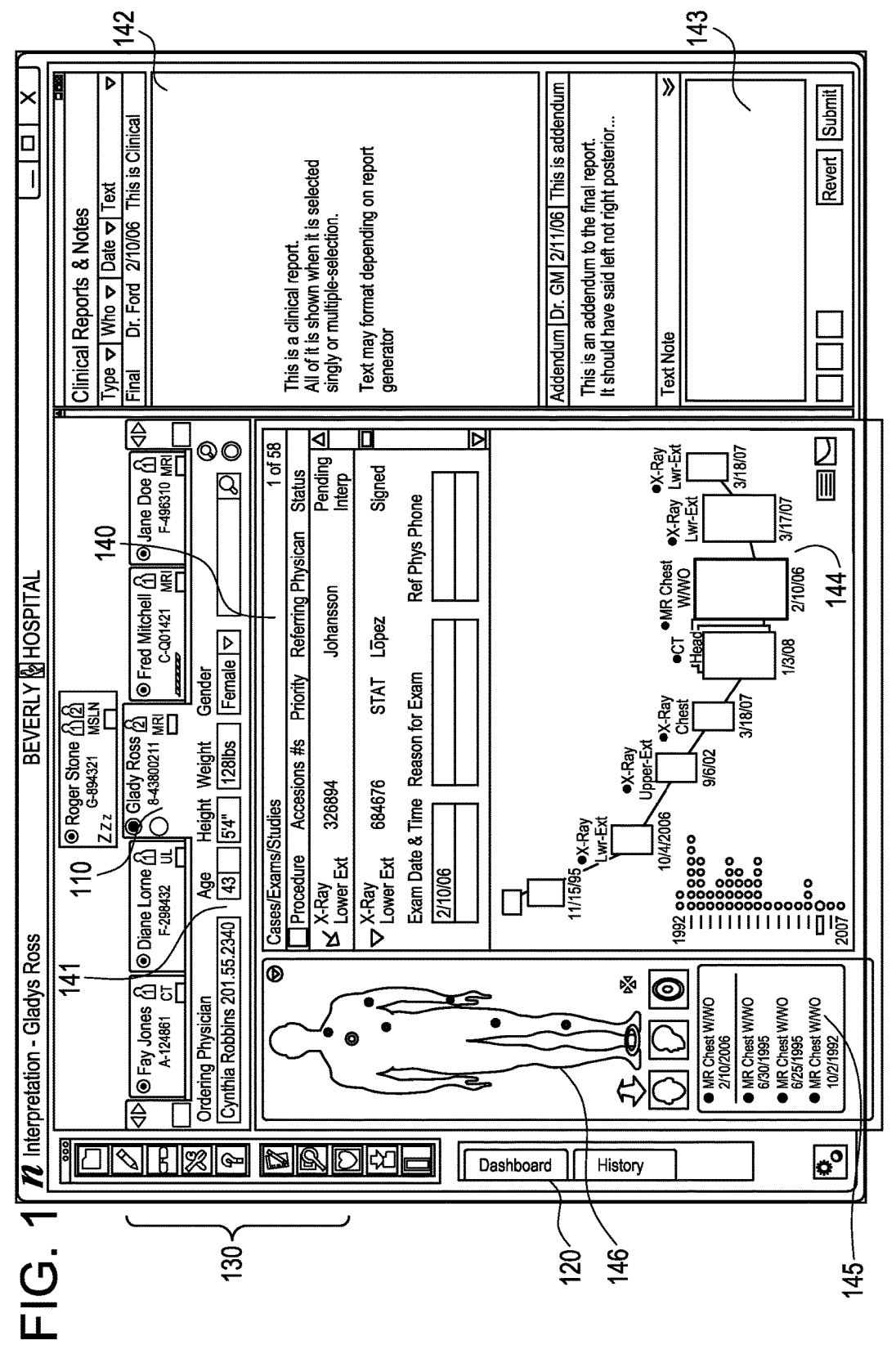

According to certain embodiments, one of a workstation's screens is used in whole or in part for display of interactive visual control called a "Workflow Manager". The workflow manager is used for presentation, search, data mining, drilling down, selection, and/or retrieval for detailed examination (including but not limited to presentation on same or other display screens) of various collateral clinical evidences varying in aspects including but not limited to: method of acquiring, method of storing, stored internally or accessed through external connections, way of presentation and analysis, among others. One particular implementation of the control is presented in FIG. 1. According certain embodiments, a graphical space of the workflow manager includes independent, yet coordinated, visual panes as demonstrated by FIG. 1.

According certain embodiments, one of such panes represents a queue of examination cases one of which is opened now, while others are pending interpretation according to their order in the worklist.

According certain embodiments, one of the presentation panes represents a history of medical events for a patient including but not limited to visits, tests, treatments, diagnostic imaging, among others, for example. The historical representation characterizes each historical period (e.g., a year) with respect to an intensity of medical events discriminating or dividing them into distinctly perceived groups. For illustrative purpose only, events may be divided into events with positive, neutral and negative outcome. The discrimination may be performed based on one or more criterion including but not limited to: shape, color, brightness, etc. Scrolling of the historical line or selection of a certain period can optionally result in focusing of one or several other panes onto one or a group of its native objects that are related to the same or a close historical period, for example. The focusing is governed by pre-defined or interactively activated rules, for example.

According to certain embodiments, one of the presentation panes includes a graphical representation of a human anatomy in one or multiple aspects including but not limited to: body parts, organs, diseases, medical subspecialties, etc. Focusing on one or more of these objects or on a group of them can optionally result in focusing of one or several other panes onto one or a group of its native objects related to the same or close anatomical aspects according to pre-defined or interactively activated rules, for example.

According to variation of the above embodiment, a style of anatomical presentation can vary to be context sensitive to various factors including but not limited to gender and/or age group of the patient, and/or selections made on other presentation panes, and/or other factors or combination of several such factors, for example.

According to certain embodiments, one of a multiplicity of the presentation panes includes a graphical representation of a multiplicity of clinical evidence displayed in an ordered and grouped manner.

Particular rule of said ordering and grouping can be set by rules—predefined, and/or context sensitive, provided that said rules can be modified and/or overruled by any interactive activity of the user in same or other panes. For exemplary purpose only we can consider that when any specific anatomy is selected in anatomical presentation pane the clinical evidences are grouped by years and ordered by historical periods, or alternatively—upon any activity in historical pane evidences become grouped by type of clinical evidences and ordered through their historical attribution. Focusing on either of these groups of objects or on either specific object can optionally result in focusing of one or several other panes onto one or group of their native objects, related to objects according to pre-defined, and/or context sensitive, and/or interactively activated rules.

According to certain embodiments, the above "evidence" representation objects or any other respective grouped and/or ungrouped object(s) on any other panes can be optionally organized as interactive ruler, carousel, and/or any other mechanical association that allows repositioning of the focus from one group of evidence onto another via a perceived "scrolling of associated mechanical representation," thus keeping the object of focus always in the middle of the order for better perception of other objects or groups of objects preceding and succeeding the object in focus.

According to a variation of the above embodiment, content of each group of evidence can be context sensitive to selections and options activated in the course of a work process and/or in other panes, for example.

According to certain embodiments, the objects representing "evidence" and/or any other respective grouped and/or ungrouped object on other pane(s) can be optionally presented in such a way that a physical size of representation and a number of details included in such presentation is dependent on proximity of an object to the object in focus. Thus, improved perception of more details in object of focus and neighboring ones is facilitated, although only a broad or "30,000 feet view" of more distant objects and/or groups of objects is given.

According to certain embodiments, focusing on any object or group of objects by hovering over an object or group of objects with a mouse cursor or any other suitable action optionally causes other inactive presentation pane(s) to focus on a drilled-down level of presentation for the object in focus on active presentation pane, thus presenting relevant properties of the highlighted object and/or group of objects. Optionally, the drill down presentation can be a plain geometrical blow-up or magnification of the same group highlighted on the active pane.

According to certain embodiments, one of the panes can be used as an organizer of the objects selected via interactions on other panes. The process of selection of the objects for the organizer can be viewed as similar to selection of merchandise into "shopping carts" on commercial websites, for example. However, usage of the objects included into the organizer is different from traditional "shopping cart checkout" and depends on a variety of factors including but not limited to the nature of the objects, continuation of the workflow, and/or rule of context sensitivity, and variety other factors and/or combination of factors, for example.

According to certain embodiments, action controls including but not limited to toolbars menus, right-click menus, mouse operation mode, and/or others can be different for different panes and/or context sensitive to variety of factors including but not limited to: actual context of the pane or some of its specific objects, and/or workflow step, etc.

According to certain embodiments, each clinical evidence or group of clinical evidences is represented by its most meaningful and diagnostically important component. For purposes of example only, assume that each diagnostic imaging study is represented by one or several of its key images, while each image series is represented by its "meaningful image" which was once included into a key images set, etc.

According to certain embodiments, each presentation pane can be frozen in its content (e.g., pinned down) and its context sensitive synchronization to other panes or workflow steps can be temporarily suspended.

According to certain embodiments, highlighting of an object and/or group of objects provides temporarily drill-down screen similar to "tooltip" postings of the Microsoft Windows® operating system.

According to certain embodiments, workflow control supports collaboration activities so that actions of independent users performed on physically different and—optionally—remotely located workstations will be replicated or otherwise synchronized towards the workstation(s) of the collaboration partner(s), thus facilitating a substantially identical flow of events and presentation instances on all workstations of collaborating parties.

According to certain embodiments, workflow and collaboration can include notifications and messaging to other parties including referring physicians.

According to certain embodiments, a chain of actions undertaken within the workflow manager including but not limited to data discovery, data search, data drill-down, data retrieval and display for examination, collaboration sessions, notifications and messaging, and/or others are logged and recorded for various purposes including but not limited to: teaching, presentation to supervisor, recollection and reproduction, guided instructions, legal recording, and/or other purposes or combination of purposes, for example.

As illustrated, for example, in FIG. 1, a graphical workflow manager 100 includes one or more patient tabs 110, one or more sections 120 for each tab 110, one or more tools 130 for use with data in the tab(s) 110, and a plurality of presentation panes 140-147 with information regarding a patient, for example.

The example workflow manager 100 shown in FIG. 1 includes an examination status or queue pane 140, a patient demographic pane 141, a clinical report pane 142, a notes pane 143, a history of events pane 144, an image or exam series pane 145, and a patient anatomy pane 146. Other embodiments may include additional panes, fewer panes, and/or other combinations of panes and corresponding information/evidence, for example. As described above, a user may select a tab 110 to view clinical evidence regarding a particular patient. Within the tab, the examination status pane 140 provides the user with a view of available cases, examinations, and/or other studies and their status (e.g., pending interpretation, reviewed, signed, etc.). The demographics pane 141 provides demographic information regarding the patient, such as age, height, weight, gender, name, ordering/referring physician, etc.

The clinical report pane 142 and the note pane 143 may be implemented together or separately and provide a user with a clinical report and notes/addendum to the report and/or other observation to be entered by a user and/or other healthcare practitioner, for example. This information can then be made available for review and/or modification via the presentation pane(s) 142, 143.

Presentation pane 144 provides a history of events, such as examinations/images, for the patient. In certain embodiments, one or more events may be selected in the pane 144 to retrieve the contents of that event (e.g., examination images and/or reports) for review.

Presentation pane 145 provides series of images/exams for a patient, for example. Pane 146 provides a graphical representation of patient anatomy. The anatomy representation may include a graphical indication of findings and/or other events/conditions for the patient, areas of image data for the patient, and/or other information, for example. Such graphical indication may include a link to additional information, may trigger display of information in another pane, and/or may prompt a user to manually retrieve additional information, for example.

In certain embodiments, sections 120 of the workflow manager 100 may provide access to additional information and/or functionality, such as patient history, dashboard information, etc.

Certain embodiments may be implemented in conjunction with an information system for a healthcare enterprise including a PACS IT system for radiology and/or other subspecialty system as demonstrated by the business and application diagram in FIG. 2. The system 200 of FIG. 2 includes a clinical application 210, such as a radiology, cardiology, opthalmology, pathology, and/or application. The system 100 also includes a workflow definition 220 for each application 210. The workflow definitions 220 communicate with a workflow engine 230. The workflow engine 230 is in communication with a mirrored database 240, object definitions 260, and an object repository 270. The mirrored database 240 is in communication with a replicated storage 250. The object repository 270 includes data such as images, reports, documents, voice files, video clips, EKG information, etc.

Figure 3:
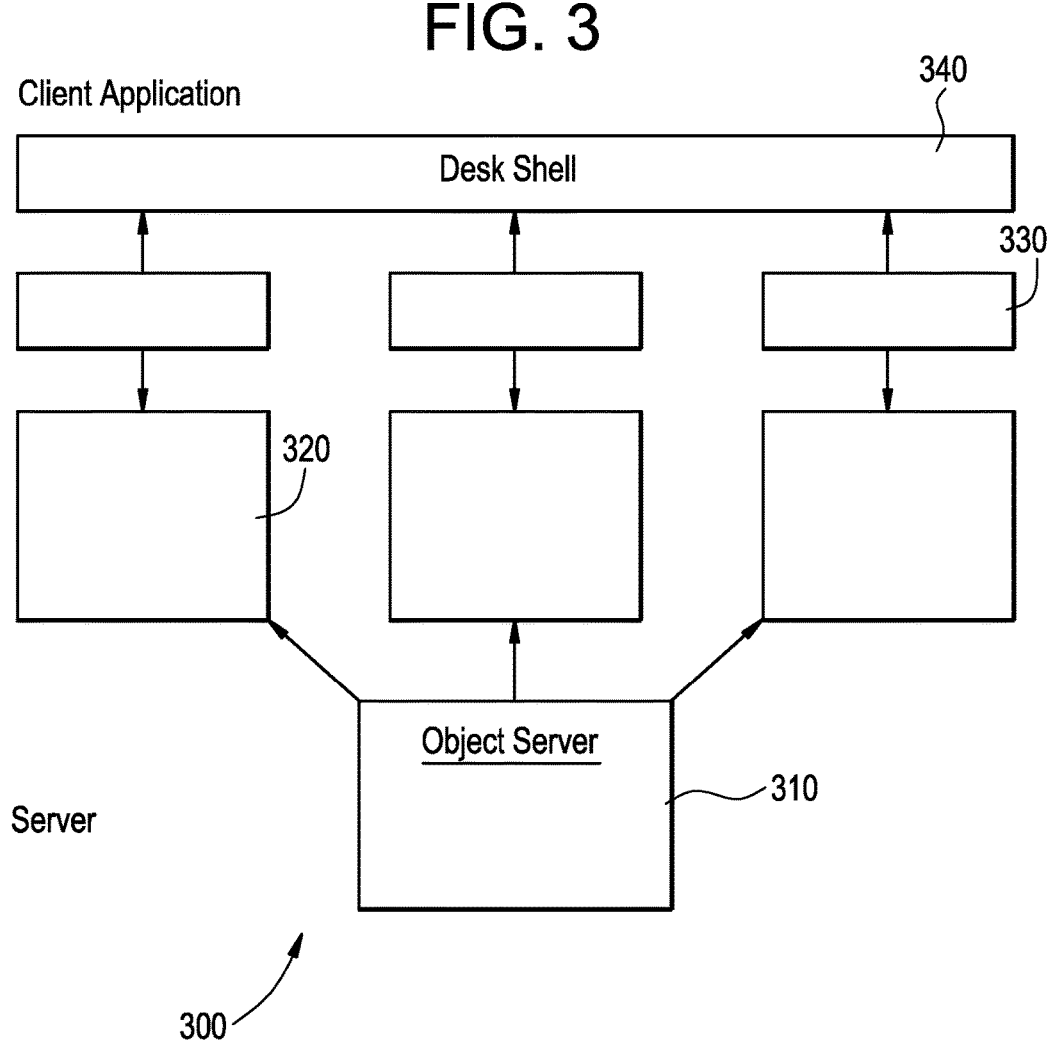
FIG. 3 illustrates an architecture of front-end components, thin and thick clients, and applications running partially on client workstations in accordance with an embodiment of the present invention.

Certain embodiments may be implemented in conjunction with an architecture of front-end components including but not limited to a Graphical User Interface (GUI), thin and thick clients, applications running partially on the client workstations, and others. One embodiment of this architecture is presented in FIG. 3. The architecture 300 of FIG. 3 provides the following definite advantages for multi-specialty system development, support and evolution. For parallel development, a system can be divided into independent applications and application modules. Modules designed for one application can be reused in other applications. There is no need to split teams based on physical tiers (e.g., a client team and a server team). An object server 310 can communicate with applications 320 and application modules 330 to provide functionality to a user via a desk shell 340 running on a client workstation. Applications 320 can run partially on a client workstation and partially on a server, for example.

Figure 4:
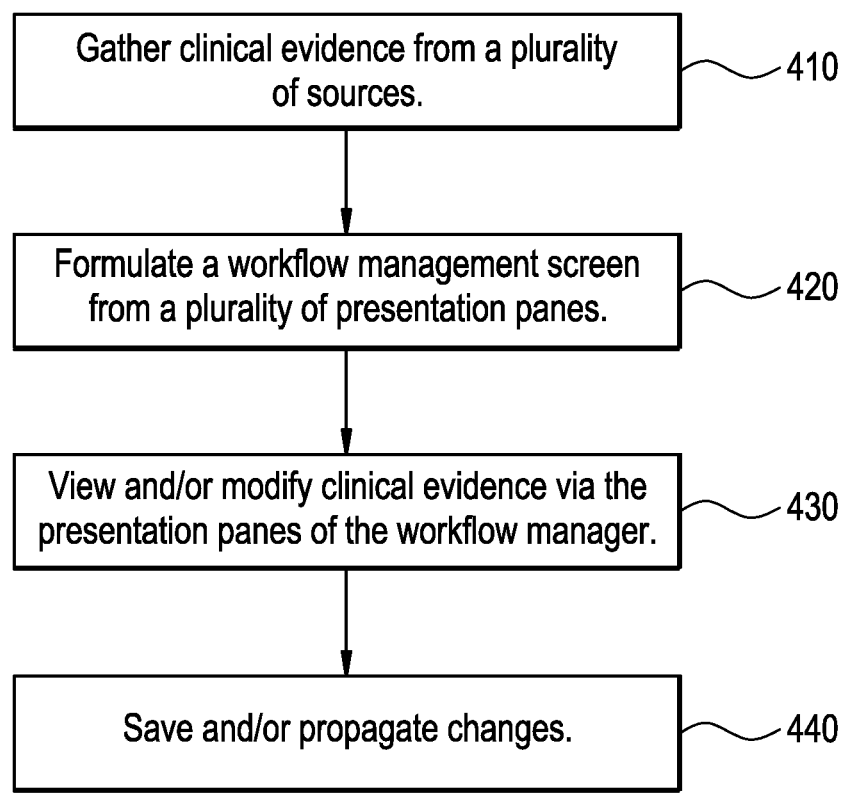
FIG. 4 shows a flow diagram for a method for presentation of clinical evidence in accordance with an embodiment of the present invention.

FIG. 4 depicts a flow diagram for a method for presentation of clinical evidence in accordance with an embodiment of the present invention. At step 410, clinical evidence is gathered from a plurality of sources. For example, clinical evidence from clinical information systems such as RIS, EMR, LIS, HIS, PACS, and/or other storage, may be aggregated for presentation to a user.

At step 420, a workflow management screen is formulated from a plurality of presentation panes. Each pane presents certain clinical evidence. The panes may correlate or be synchronized to provide different evidence related to a particular patient, clinical practitioner, healthcare enterprise, etc. As described above, one or more panes may be context sensitive and may provide various perspectives on the clinical data.

At step 430, clinical evidence and/or other data may be viewed and/or modified via the presentation panes of the workflow manager. For example, images, findings, and the like may be highlighted, retrieved, magnified, etc., based on information presented in the panes of the workflow manager interface. Clinical evidence and/or related findings may be modified, such as through generation of a report and/or notes regarding an image study. At step 440, any changes may be saved and/or propagated to other systems.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 5:
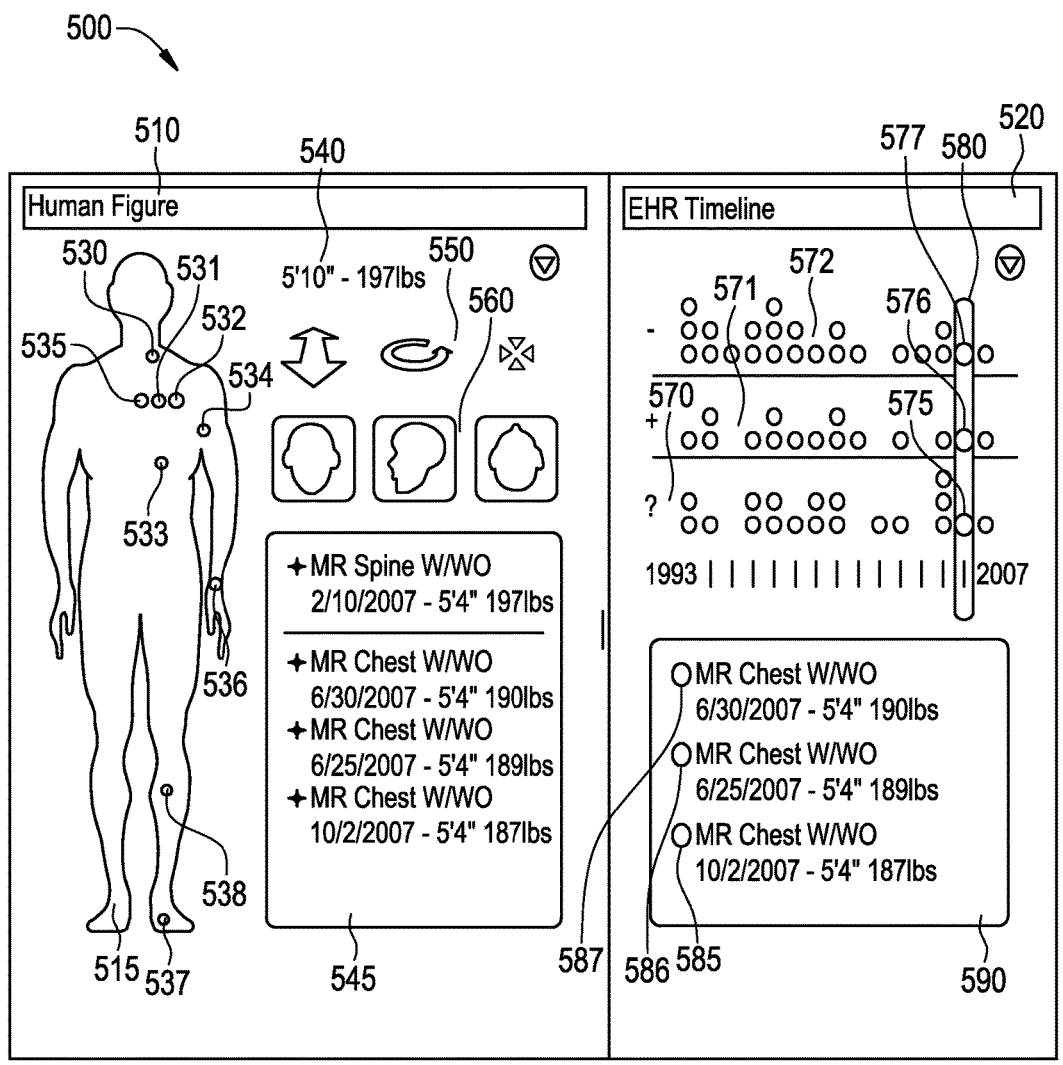
FIG. 5 illustrates an example graphical patient interface system providing access to patient clinical and support information via a representation of a human figure and a corresponding electronic health record timeline in accordance with certain embodiments of the present invention.

FIG. 5 illustrates an example graphical patient interface system 500 providing access to patient clinical and support information via a representation of a human figure and a corresponding EHR timeline in accordance with certain embodiments of the present invention. The system 500 includes a human figure portion 510 and an EHR timeline portion 520. The portions 510 and 520 can be implemented as separate and/or as integrated components of the interface system 500. Components of the system 500 can be implemented separately and/or integrated in various forms via hardware, software, and/or firmware, for example.

The human figure portion 510 includes a graphical anatomic representation 515, which includes one or more indicators 530-538. The human figure portion 510 also includes identification information 540 for the patient, one or more imaging studies and/or other source documents 545, one or more orientation/viewing tools 550, and one or more image view selectors 565, for example. Using the indicators 530-538 and/or source document information 545, a user can retrieve associated event documents, such as imaging studies, lab results, patient reports, etc., for further review, for example. In certain embodiments, a user mouse over or other cursor positioning over an indicator 530-538 displays a thumbnail of the corresponding document.

The EHR timeline portion 520 includes one or more parallel timelines 570-572 of patient events, such as image studies. One or more indicators 575-577, similar to the indicators 530-538, represent imaging studies and/or other documented events that have occurred in the diagnosis and treatment of the patient. These indicators 575-577 are positioned together or in separate groups (as depicted in FIG. 5) along the timeline(s) 570-572. A time bar 580 can be manipulated by a user along the timeline(s) 570-572 to access imaging studies and/or other documents corresponding to indicator(s) 575-577 at that date. Positioning the time bar 580 at a point along the timeline(s) 570-572 at indicators 575-577 displays link(s) and/or other information 585-587 regarding imaging studies and/or other documents in a documents area 590. Using the indicators 575-577 and/or links 585-587 in the documents area 590, a user can retrieve documents corresponding to the links 585-587 for further review, for example. In certain embodiments, a user mouse over or other cursor positioning over an indicator 575-577 displays a thumbnail of the corresponding document.

Indicators 530-538 can be used with the representation 515 of a human figure to illustrate what procedures and/or examinations a patient has undergone, what anatomical part they were applied to, and what result (e.g., pathology) was found. Data from a plurality of clinical sources can be aggregated for display via indicators 530-538 on the anatomical representation 515. In certain embodiments, each indicator 530-538 (e.g., a circle or dot shown on the anatomical outline of FIG. 5) indicates a procedure/exam, and a coloration of the indicator can be used to visually indicate an outcome of the procedure/exam diagnosis (e.g., good, bad, unknown, etc.). A user then can drill down into each of the indicators 530-538 to retrieve and review additional detail. A user can hover over or click on an indicator 530-538, for example, and see a corresponding report, image, etc. A user can also review the EHR timeline 520 to see the indicator 575-577 dots/outcomes over time on the timelines 570-572. Together, the human figure portion 510 and the EHR timeline portion 520 serve as an anatomical dashboard. While the anatomic representation 515 shown in FIG. 5 is a two-dimensional ("2D") outline of a human figure, the representation 515 can be a human figure, heart, lung, etc. In certain embodiments, the representation 515 can be a 3D representation of a body, certain body part, etc.

Additionally, when a user moves a cursor to an indicator 530-538 on the anatomical representation 515, the timeline(s) 570-572 can be correspondingly scrolled and vice versa (e.g., selecting an indicator 575-577 on a timeline 570-572 can highlight and/or otherwise affect an indicator 530-538 on the human FIG. 515. In certain embodiments, the timeline(s) 570-572 can be combined (e.g., overlaid) with the human FIG. 515, so the user sees a time series of the body or part itself, for example.

In certain embodiments, relationships between patient events, such as imaging studies and examinations, can be provided and/or deduced from information in patient data messages, for example. Event relationship information can be used to provide clinical decision support in addition to the timeline and graphical representation of events. Thus, an order in time, an affected anatomy, and a relationship between events can be provided via the interface 500.

Patient data can be found in HL7 messages, in DICOM information, in structured reports, and/or in other single and/or aggregated formats. Data is received from a variety of clinical information systems, including RIS, PACS, CVIS, EMR, lab, physical exams, etc. Anatomical structure and laterality can be extracted from message data, such as HL7 messages data. Relationship information can be extracted and/or deduced from an analysis of procedure timing and outcome according to certain guidelines/rules, for example. For example, for a procedure one and procedure two, if decision support rules indicate that procedure two follows a positive result in procedure one, the system 500 can deduce that procedure one had a positive diagnosis. However, an unrelated procedure two following procedure one may indicate that the result of procedure one was negative because procedure two does not fit the procedure pattern. As another example, if procedure two was a surgical operation and procedure one was a PET CT image series, then the system can presume that the surgical procedure was done to remove cancer found in a positive diagnosis from procedure one. If procedure two is the same procedure as procedure one but is six months later in time, then the system can deduce that procedure two is probably a follow up for a diagnosis made in procedure one, for example. Extracted and deduced patient and procedure information from one or more clinical sources can be used to construct the interface 500 depicted in FIG. 5, for example.

Figure 6:
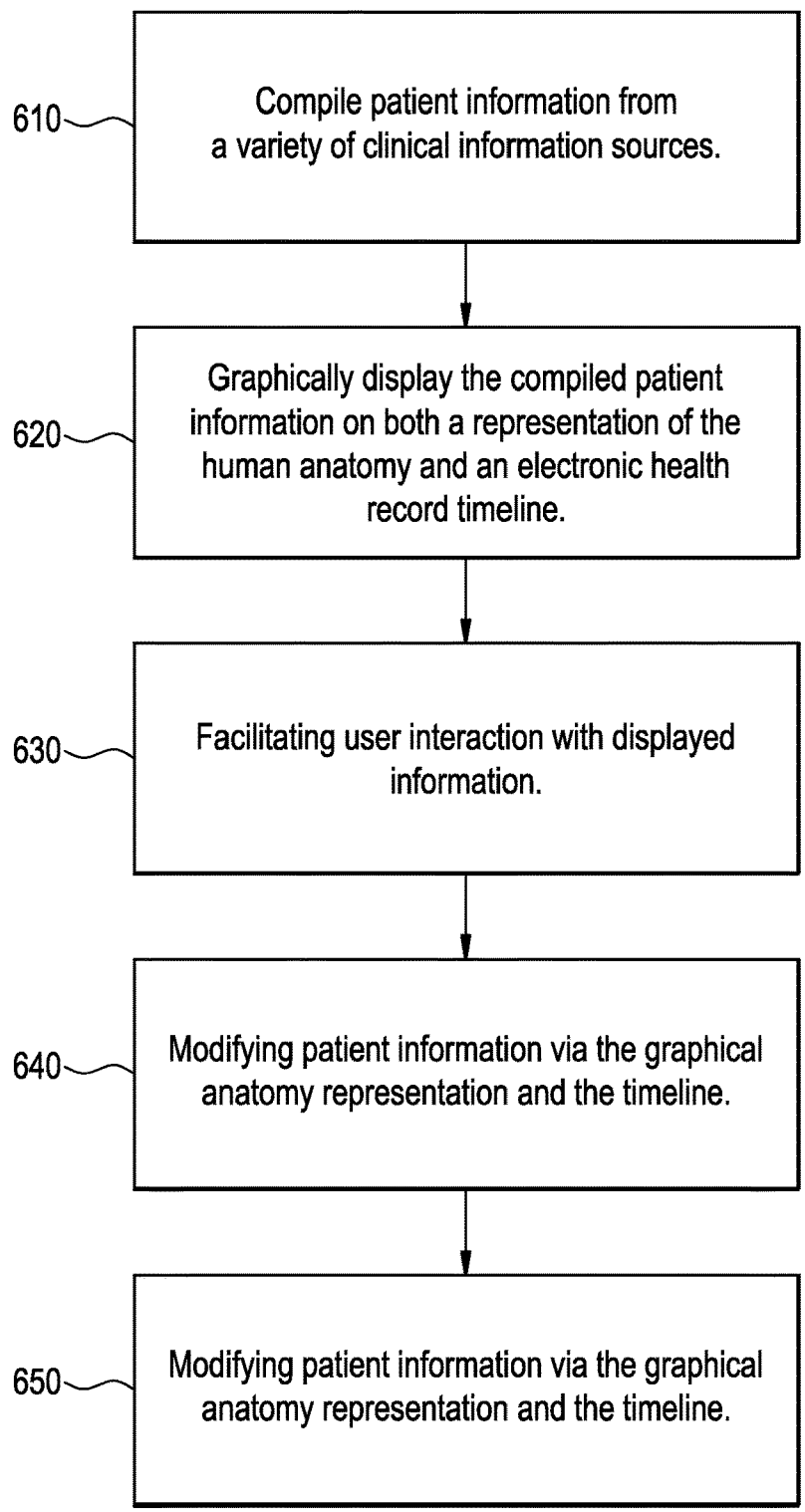
FIG. 6 depicts a flow diagram for a method for display of and interaction with patient clinical information in accordance with certain embodiments of the present invention.

FIG. 6 depicts a flow diagram for a method for display of and interaction with patient clinical information in accordance with certain embodiments of the present invention. At 610, patient information is compiled from a variety of clinical information sources. For example, patient information, including patient image studies and/or other data, can be extracted and/or deduced from clinical information system messages being transmitted.

At 620, the compiled patient information is graphically displayed on both a representation of the human anatomy (e.g., an outline of the human figure) and a patient EHR timeline. For example, corresponding indicators (e.g., the indicators 530-538 and 575-577 shown in FIG. 5) can be shown on both a graphical anatomical representation (e.g., the representation 515 of FIG. 5) and an EHR timeline (e.g., the timeline(s) 570-572 of FIG. 5) and made available for user interaction. The indicators on both the graphical anatomy and the EHR timeline can be linked such that an action in one panel produces a corresponding action in the other panel, for example.

At 630, a user can interact with information depicted on the graphical anatomy and/or the EHR timeline. For example, a user can position a cursor over an indicator on the human figure and/or the timeline to display a thumbnail version of a corresponding document, such as an image, a report, an order, etc. A user can select an indicator to retrieve a full version of the document, for example. A user can select an indicator on the human figure anatomical representation, and the EHR timeline advances to a point in time at which that event occurred, for example. The user can then see what other events occurred for that patient on the same day and/or nearby days, for example. A user can select an indicator on the timeline, and a corresponding indicator on the graphical anatomical representation will be highlighted to the user, for example. As another example, a user can select a certain type of imaging exam and all indicators corresponding to that type of exam will be highlighted.

At step 640, clinical evidence and/or other data can be modified via the graphical anatomy representation and/or the EHR timeline. For example, images, findings, and the like may be highlighted, annotated, etc. Clinical evidence and/or related findings can be modified, such as through generation of a report and/or notes regarding an image study. At step 650, any changes can be saved and/or propagated to other system(s).

One or more of the steps of the method 600 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments provide a technical effect of graphically presenting patient health information with respect to particular anatomic structure over time. Certain embodiments provide a multi-specialty graphical representation of a patient's health record in both anatomic and historical context. Whereas prior approaches presented a user with difficulty in viewing a patient's record even when all available data was present and provided no facility for determining a severity of chronic patient issues, certain embodiments help a user to grasp a full extent of a patient's current and past health without manually searching through multiple systems.

It should be understood by any experienced in the art that the inventive elements, inventive paradigms and inventive methods are represented herein by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

For example, certain embodiments may be implemented as a computer readable medium having a set of instructions for execution on a computing device and a processor for executing the set of instructions on the computer readable medium. The set of instructions includes a workflow management routine aggregating clinical evidence from a plurality of information sources. The set of instructions also includes a workflow screen routine generating a plurality of presentation panes. Each of the plurality of presentation panes displays at least a portion of the clinical evidence according to a particular perspective. The plurality of presentation panes are independent but coordinated. Each of the plurality of presentation panes is context sensitive. In certain embodiments, the workflow management routine facilitates one or more of data searching, data mining, and presentation of clinical evidence data at varying levels of granularity in conjunction with the plurality of presentation panes, for example.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A patient information interface system presenting an aggregated, graphical view of patient anatomy and history via a graphical user interface, the graphical user interface displayed on a workstation screen, said system comprising:
  a processor configured to at least extract data for a patient from a plurality of messages received from a plurality of clinical information sources, identify one or more relationships between patient events related to medical conditions based on the data, compile the data, and convert the data into an anatomical dashboard including a first area and a second area displayed concurrently for interaction via the graphical user interface, the interaction including modifying the data by generating a report, the first and the second areas to produce a capability to determine a severity within an anatomic structure for the patient with respect to time, the anatomical dashboard including:
  a graphical representation, generated from the extracted data and displayed via the graphical user interface in the first area, visually depicting at least a portion of a human anatomy and including one or more indicators corresponding to clinical events that have occurred in connection with the patient, each of the one or more indicators located and displayed at an anatomical location on the graphical representation that corresponds to an anatomy of the patient affected by the clinical event corresponding to the respective indicator, each of the one or more indicators visually indicating a deduction based on the one or more relationships, the deduction including a diagnosis to support a clinical decision; and
  an electronic health record timeline of clinical events for the patient, generated from the extracted data and displayed via the graphical user interface in the second area, the timeline including the one or more indicators corresponding to clinical events that have occurred in connection with the patient, the one or more indicators displayed on both the graphical representation in the first area of the graphical user interface and the electronic health record timeline in the second area of the graphical user interface,
  wherein patient information based on the converted data and the one or more identified relationships is displayed on both a) the graphical representation of at least a portion of the human anatomy in the first area of the graphical user interface and b) the electronic health record timeline in the second area of the graphical user interface, and wherein a user can interact with and modify the patient information via either of a) the graphical representation of at least a portion of the human anatomy and b) the electronic health record timeline to trigger a corresponding modification on the other of a) the graphical representation of at least a portion of the human anatomy in the first area of the graphical user interface and b) the electronic health record timeline in the second area of the graphical user interface,
wherein modifying the patient information includes a selection or a change of an indicator on one of a) the graphical representation or b) the electronic health record timeline, the modification activating the processor to generate the report and propagate the modification to one or more other systems.

2. The system of claim 1, wherein the one or more indicators are provided from one or more of the plurality of clinical information sources and are deduced from information in clinical data messages from one or more of the plurality of clinical information sources.

3. The system of claim 1, wherein the time bar is positionable by a user at a certain point along the electronic health record timeline to display information regarding one or more clinical events for the patient occurring at that point in the timeline.

4. The system of claim 1, wherein selection of one of the one or more indicators on either the graphical representation or the electronic health record timeline displays a document corresponding to the clinical event for the patient.

5. The system of claim 1, wherein positioning a cursor over one of one or more indicators on either the graphical representation or the electronic health record timeline displays a thumbnail view of a document corresponding to the clinical event for the patient.

6. The system of claim 1, wherein the graphical representation comprises a three-dimensional representation of at least a portion of a human anatomy.

7. The system of claim 1, wherein the electronic health record timeline is overlaid on the graphical representation for joint manipulation of the one or more indicators of the graphical representation and the electronic health record timeline.

8. The system of claim 1, wherein a characteristic of the one or more indicators indicates at least one of a type, a status, and a severity of the clinical event corresponding to the indicator.

9. The system of claim 1, further comprising a control to allow a user to manipulate a view of the graphical representation.

10. The system of claim 1, wherein the electronic health record timeline is overlaid on the graphical representation and is configured to generate a time series of images for the at least a portion of the human anatomy based on a selected indicator on the graphical representation and a position of the time bar with respect to the electronic health record timeline and the selected indicator, the time series of images shown with respect to the selected indicator in the graphical representation.

11. A computer-implemented method for aggregating and displaying a graphical view of patient anatomy and history via a graphical user interface, the graphical user interface displayed on a workstation screen, said method comprising:
extracting patient information from a plurality of messages received from a plurality of clinical information sources and identifying clinical events related to a patient based on the patient information;
identifying one or more relationships between patient events related to medical conditions based on the patient information;
compiling the patient information with the one or more relationships related to the medical conditions;
graphically displaying, via the graphical user interface, an anatomical dashboard formed using the compiled patient information with the one or more relationships, the anatomical dashboard including a first area and a second area displayed concurrently for interaction via the graphical user interface, the interaction including modifying the patient information by generating a report, the first and the second areas to produce a capability to determine a severity within an anatomic structure for the patient with respect to time, the anatomical dashboard including: a) a graphical representation visually depicting at least a portion of a human anatomy displayed in the first area and b) an electronic health record timeline of clinical events for the patient displayed in the second area, each of the graphical representation and the electronic health record timeline including corresponding sets of one or more indicators identifying clinical events that have occurred in connection with the patient, each of the one or more indicators located at an anatomical location on the graphical representation that corresponds to an anatomy of the patient affected by the clinical event corresponding to the respective indicator and located on the electronic health record timeline at a point in time at which the clinical event occurred, wherein each of the one or more indicators indicate a deduction based on the one or more relationships, the deduction including a diagnosis to support a clinical decision, wherein the electronic health record timeline comprises a plurality of parallel timelines, each of the timelines indicating a different type of clinical event occurring with respect to the patient; and
facilitating user interaction with the displayed patient clinical event indicators on both the graphical representation and the timeline via the graphical user interface, wherein patient information is displayed on both a) the graphical representation of at least a portion of the human anatomy and b) the electronic health record timeline and wherein a user can interact with and modify the patient information via either of a) the graphical representation of at least a portion of the human anatomy and b) the electronic health record timeline, wherein modifying the patient information includes activating a workflow engine to generate the report and propagate the modification to one or more other systems.

12. The method of claim 11, further comprising deducing a relationship between clinical events based on information in clinical data messages from one or more of the plurality of clinical information sources.

13. The method of claim 11, wherein user interaction comprises positioning the time bar at a certain point along the electronic health record timeline to display information regarding one or more clinical events for the patient occurring at that point in the timeline.

14. The method of claim 11, further comprising displaying a document corresponding to the clinical event for the patient based on selection by a user of one of the one or more indicators on either the graphical representation or the electronic health record timeline.

15. The method of claim 11, further comprising displaying a thumbnail view of a document corresponding to the clinical event for the patient based on positioning by a user of a cursor over one of one or more indicators on either the graphical representation or the electronic health record timeline.

16. The method of claim 11, wherein the electronic health record timeline is overlaid on the graphical representation for joint manipulation of the one or more indicators of the graphical representation and the electronic health record timeline.

17. The method of claim 11, wherein a characteristic of the one or more indicators indicates at least one of a type, a status, and a severity of the clinical event corresponding to the indicator.

18. The method of claim 11, wherein facilitating user interaction further comprises allowing a user to manipulate a view of the graphical representation.

19. The method of claim 11, wherein the electronic health record timeline is overlaid on the graphical representation and is configured to generate a time series of images for the at least a portion of the human anatomy based on a selected indicator on the graphical representation and a position of the time bar with respect to the electronic health record timeline and the selected indicator, the time series of images shown with respect to the selected indicator in the graphical representation.

20. A non-transitory machine readable medium having a set of instructions for execution on a computing device, the set of instructions, when executed on the computing device, causing the computing device to execute a method for aggregating and displaying a graphical view of patient anatomy and history via a graphical user interface, the graphical user interface displayed on a workstation screen, the method comprising:

extracting patient information from a plurality of messages received from a plurality of clinical information sources and identifying clinical events related to a patient based on the patient information;

identifying one or more relationships between patient events related to medical conditions based on the patient information;

compiling the patient information with the one or more relationships related to the medical conditions;

graphically displaying, via the graphical user interface, an anatomical dashboard formed using the compiled patient information with the one or more relationships, the anatomical dashboard including a first area and a second area displayed concurrently for interaction via the graphical user interface, the interaction including modifying the patient information by generating a report, the first and the second areas to produce a capability to determine a severity within an anatomic structure for the patient with respect to time, the anatomical dashboard including: a) a graphical representation visually depicting at least a portion of a human anatomy displayed in the first area and b) an electronic health record timeline of clinical events for the patient displayed in the second area, each of the graphical representation and the electronic health record timeline including corresponding sets of one or more indicators identifying clinical events that have occurred in connection with the patient, each of the one or more indicators located at an anatomical location on the graphical representation that corresponds to an anatomy of the patient affected by the clinical event corresponding to the respective indicator and located on the electronic health record timeline at a point in time at which the clinical event occurred, wherein each of the one or more indicators indicate a deduction based on the one or more relationships, the deduction including a diagnosis to support a clinical decision, wherein the electronic health record timeline comprises a plurality of parallel timelines, each of the timelines indicating a different type of clinical event occurring with respect to the patient; and facilitating user interaction with the displayed patient clinical event indicators on both the graphical representation and the timeline via the graphical user interface, wherein patient information is displayed on both a) the graphical representation of at least a portion of the human anatomy and b) the electronic health record timeline and wherein a user can interact with and modify the patient information via either of a) the graphical representation of at least a portion of the human anatomy and b) the electronic health record timeline, wherein modifying the patient information includes activating a workflow engine to generate the report and propagate the modification to one or more other systems.

* * * * *